(12) United States Patent
Klassen

(10) Patent No.: US 12,315,607 B2
(45) Date of Patent: May 27, 2025

(54) PORTABLE NON-VOLATILE STORAGE DEVICE FOR USE IN PROVIDING PATIENT MEDICAL RECORDS REGARDLESS OF PATIENT'S LEVEL OF CONSCIOUSNESS

(71) Applicant: Doug Klassen, Holland, MI (US)

(72) Inventor: Doug Klassen, Holland, MI (US)

( * ) Notice: Subject to any disclaimer, the term of this patent is extended or adjusted under 35 U.S.C. 154(b) by 479 days.

(21) Appl. No.: 17/705,800

(22) Filed: Mar. 28, 2022

(65) Prior Publication Data
US 2023/0307105 A1    Sep. 28, 2023

(51) Int. Cl.
*G16H 10/65* (2018.01)
*G06F 3/06* (2006.01)

(52) U.S. Cl.
CPC .......... *G16H 10/65* (2018.01); *G06F 3/0604* (2013.01); *G06F 3/0629* (2013.01); *G06F 3/0679* (2013.01)

(58) Field of Classification Search
CPC ..... G16H 10/65; G06F 3/0604; G06F 3/0629; G06F 3/0679
See application file for complete search history.

(56) References Cited

U.S. PATENT DOCUMENTS

| | | | |
|---|---|---|---|
| 8,938,655 B2 | 1/2015 | Hamilton et al. | |
| 9,448,868 B2 | 9/2016 | Liang | |
| 9,899,096 B2 | 2/2018 | Kim | |
| 10,488,892 B1* | 11/2019 | Lin | H05K 7/20145 |
| 10,990,521 B1 | 4/2021 | Hwang | |
| 11,037,625 B2 | 6/2021 | Peddle et al. | |
| 11,080,181 B1 | 8/2021 | Kuzmin et al. | |
| 11,647,967 B2* | 5/2023 | Selvaraj | A61B 5/7221 702/179 |
| 2007/0143569 A1 | 6/2007 | Sanders et al. | |
| 2008/0319799 A1* | 12/2008 | Knowlton | G16H 10/65 705/3 |
| 2009/0076849 A1* | 3/2009 | Diller | G16H 10/65 705/3 |
| 2009/0112627 A1* | 4/2009 | Berkman | G16H 10/65 705/51 |
| 2009/0281836 A1* | 11/2009 | Velarde | G16H 10/65 707/999.102 |
| 2011/0256024 A1* | 10/2011 | Cole | A61B 5/0022 422/68.1 |
| 2012/0179908 A1* | 7/2012 | Duma | G16H 10/65 713/165 |
| 2013/0080680 A1 | 3/2013 | Chu | |
| 2014/0101371 A1 | 4/2014 | Nguyen et al. | |
| 2014/0334089 A1* | 11/2014 | Schade | G06F 1/183 361/679.32 |
| 2015/0248235 A1* | 9/2015 | Offenberg | G06F 3/0237 715/773 |

(Continued)

*Primary Examiner* — An T Nguyen
(74) *Attorney, Agent, or Firm* — King & Partners, PLC

(57) ABSTRACT

A portable non-volatile storage device, including: (a) a housing assembly, wherein the housing assembly includes: at least one sidewall, a top wall, and a bottom wall; and wherein the at least one sidewall, the top wall, and the bottom wall are in a spaced-apart relationship to define an internal chamber therebetween; and (b) an electronics assembly positioned at least partially within the housing assembly, wherein the electronics assembly includes: an energy source, a printed circuit board, a memory module, a sound level meter, an accelerometer, a transducer, a light source, and a user interface.

2 Claims, 8 Drawing Sheets

(56) References Cited

U.S. PATENT DOCUMENTS

| | | | | |
|---|---|---|---|---|
| 2015/0332031 | A1* | 11/2015 | Mistry | H04W 12/06 |
| | | | | 726/19 |
| 2019/0122531 | A1* | 4/2019 | Harris | H04N 23/90 |
| 2020/0383172 | A1* | 12/2020 | McCracken | H04W 88/06 |
| 2021/0272629 | A1* | 9/2021 | Peddle | G06F 12/08 |
| 2022/0386090 | A1* | 12/2022 | Temkin | H04L 67/52 |

\* cited by examiner

PORTABLE NON-VOLATILE STORAGE DEVICE FOR USE IN PROVIDING PATIENT MEDICAL RECORDS REGARDLESS OF PATIENT'S LEVEL OF CONSCIOUSNESS

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO A SEQUENCE LISTING

Not applicable.

BACKGROUND OF THE INVENTION

1. Field of the Invention

The present invention relates in general to portable non-volatile storage devices (e.g., solid state drives, flash drives, etcetera) that enable a patient to provide a physician with his/her patient information and/or medical records regardless of his/her level of consciousness (e.g., conscious, confused, delirious, somnolent, obtunded, stuporous, comatose, etcetera).

2. Background Art

Properly treating a patient, especially in emergency situations, ideally involves obtaining a complete medical history (e.g., patient allergies, current medications, comorbidities, previous medical events, the patient's treatment desires and medical directives, etcetera). Simply put, providing a physician with accurate information can mean the difference between life and death. Unfortunately, not every patient can walk into the emergency room fully conscious and timely provide his/her medical history and/or treatment desires. For example, patients that fall, have heart attacks, strokes, and/or are involved in serious accidents are often brought into the emergency room in either a diminished and/or unconscious state. The portable non-volatile storage devices of the present invention enable a patient to provide a physician with his/her patient information and/or medical records regardless of his/her level of consciousness. The portable devices of the present invention also can alert appropriate personnel that a medical event has occurred.

Portable non-volatile media and storage devices have been known in the art for years and are the subject of several patents and publications, including: U.S. Pat. No. 11,080,181 entitled "Flash Memory Drive that Supports Export of Erasable Segments," U.S. Pat. No. 11,037,625 entitled "Solid State Drive Architectures," U.S. Pat. No. 10,990,521 entitled "Data Storage System, Data Storage Device and Management Method Thereof," U.S. Pat. No. 9,899,096 entitled "NAND Flash Memory Having Multiple Cell Substrates," U.S. Pat. No. 9,448,868 entitled "Data Storing Method, Memory Control Circuit Unit and Memory Storage Apparatus," U.S. Pat. No. 8,938,655 entitled "Extending Flash Memory Data Retention Via Rewrite Refresh," United States Patent Application Publication Number 2021/0272629 entitled "Solid State Drive Architectures," United States Patent Application Publication Number 2014/0101371 entitled "Systems and Methods for Nonvolatile Memory Performance Throttling," United States Patent Application Publication Number 2013/0080680 entitled "Memory Storage Device, Memory Controller, and Temperature Management Method," and United States Patent Application Publication Number 2007/0143569 entitled "Non-Volatile Solid-State Memory Controller"—all of which are hereby incorporated herein by reference in their entirety including all references cited therein.

U.S. Pat. No. 11,080,181 appears to disclose a host-controller cooperation in managing NAND flash memory. The controller maintains information for each erase unit which tracks memory usage. This information assists the host in making decisions about specific operations, for example, initiating garbage collection, space reclamation, wear leveling or other operations. For example, metadata can be provided to the host identifying whether each page of an erase unit has been released, and the host can specifically then command each of consolidation and erase using direct addressing. By redefining host-controller responsibilities in this manner, much of the overhead association with FTL functions can be substantially removed from the memory controller, with the host directly specifying physical addresses. This reduces performance unpredictability and overhead, thereby facilitating integration of solid state drives (SSDs) with other forms of storage. The disclosed techniques are especially useful for direct-attached and/or network-attached storage.

U.S. Pat. No. 11,037,625 appears to disclose a solid state drive (SSD) that includes dynamic random access memory (DRAM), flash memory, and a solid state drive (SSD) controller. The solid state drive (SSD) also includes a peripheral component interconnect express (PCIe) bus to connect the SSD to a computing device such that a central processing unit (CPU) of the computing device exclusively reads data from, and writes data to, the DRAM. The SSD controller writes data to the flash memory from the DRAM independently of received commands from the computing device.

U.S. Pat. No. 10,990,521 appears to disclose a management method for a data storage device that includes the following steps: obtaining a plurality of association rules according to a plurality of previous access commands; building a plurality of look-up tables according to the association rules; receiving a current access command and determining whether the current access command corresponds to at least one of the look-up tables to obtain physical addresses of the current access command from the corresponding look-up table; predicting a look-up table corresponding to a subsequent access command based on these association rules; and pre-establishing the predicted look-up tables. The invention also provides a data storage system and a data storage device, which can implement the management method described above.

U.S. Pat. No. 9,899,096 appears to disclose a NAND flash memory bank having a plurality of bit lines of a memory array connected to a page buffer, where NAND cell strings connected to the same bit line are formed in at least two well sectors. At least one well sector can be selectively coupled to an erase voltage during an erase operation, such that unselected well sectors are inhibited from receiving the erase voltage. When the area of the well sectors decrease, a corresponding decrease in the capacitance of each well sector results. Accordingly, higher speed erasing of the NAND flash memory cells relative to a single well memory bank is obtained when the charge pump circuit drive capacity remains unchanged. Alternately, a constant erase speed corresponding to a single well memory bank is obtained by matching a well segment having a specific area to a charge pump with reduced drive capacity. A reduced drive capacity charge pump will occupy less semiconductor chip area, thereby reducing cost.

U.S. Pat. No. 9,448,868 appears to disclose a data storing method, a memory control circuit unit, and a memory storage apparatus. The method includes recording a bit error count of every predetermined area of every physical erasing unit and determining whether the bit error count of one of the predetermined areas of the physical programming unit of the physical erasing unit is more than a threshold bit error count. If the bit error count of one of the predetermined areas of the physical programming unit of the physical erasing unit is more than the threshold bit error count, the method also includes storing data under a second programming mode after an erasing operation is performed on the physical easing unit. Accordingly, defective physical erasing units may be effectively employed to prolong the lifespan of the memory storage apparatus.

U.S. Pat. No. 8,938,655 appears to disclose an extended data retention of flash memory devices by program state rewrite. By way of example, a memory cell or group of memory cells can be evaluated to determine a program state of the cell(s). If the cell(s) is in a program state, as opposed to a natural or non-programmed state, a charge level, voltage level and/or the like can be rewritten to a default level associated with the program state, without erasing the cell(s) first. Accordingly, conventional mechanisms for refreshing cell program state that require rewriting and erasing, typically degrading storage capacity of the memory cell, can be avoided. As a result, data stored in flash memory can be refreshed in a manner that mitigates loss of memory integrity, providing substantial benefits over conventional mechanisms that can degrade memory integrity at a relatively high rate.

United States Patent Application Publication Number 2021/0272629 appears to disclose a solid state drive (SSD) that includes dynamic random access memory (DRAM), flash memory, and a solid state drive (SSD) controller. The solid state drive (SSD) also includes a peripheral component interconnect express (PCIe) bus to connect the SSD to a computing device such that a central processing unit (CPU) of the computing device exclusively reads data from, and writes data to, the DRAM. The SSD controller writes data to the flash memory from the DRAM independently of received commands from the computing device.

United States Patent Application Publication Number 2014/0101371 appears to disclose systems and methods for nonvolatile memory ("NVM") performance throttling. Performance of an NVM system may be throttled to achieve particular data retention requirements. In particular, because higher storage temperatures tend to reduce the amount of time that data may be reliably stored in an NVM system, performance of the NVM system may be throttled to reduce system temperatures and increase data retention time.

United States Patent Application Publication Number 2013/0080680 appears to disclose a temperature management method suitable for a memory storage device having a rewritable non-volatile memory module and a memory controller used for controlling the rewritable non-volatile memory module. The temperature management method includes detecting and determining whether the hot-spot temperature of the memory storage device is higher than a predetermined temperature; and when affirmative, making the memory controller execute a cooling process, so as to reduce the hot-spot temperature of the memory storage device. Accordingly, the problem of heat buildup of the (rewritable non-volatile) memory storage device can be mitigated, as well as the problems of data loss and device aging of the (rewritable non-volatile) memory storage device.

United States Patent Application Publication Number 2007/0143569 appears to disclose a controller that includes a volatile random access memory and translation hardware. The volatile random access memory includes a table having at least one entry. The at least one entry includes a portion of a physical address of a memory location at a NAND flash non-volatile solid-state memory. The volatile random access memory is accessible to the translation hardware. The translation hardware is configured to sum binary data bits of a portion of a logical address and a pointer value to determine a random access memory address of the at least one entry and is configured to determine the portion of the physical address of the memory location at the NAND flash non-volatile solid-state memory based at least in part on the random access memory address of the at least one entry.

While the above-identified patents and publications do appear to disclose various portable media storage devices, they remain non-desirous and/or problematic inasmuch as, among other things, none of the above-identified storage devices enable a patient to provide a physician with his/her patient information and/or medical records regardless of his/her level of consciousness.

These and other objects of the present invention will become apparent in light of the present specification, claims, and drawings.

SUMMARY OF THE INVENTION

The following presents a simplified summary in order to provide a basic understanding of some aspects of the claimed subject matter. This summary is not an extensive overview, and is not intended to identify key/critical elements or to delineate the scope of the claimed subject matter. Its purpose is to present some concepts in a simplified form as a prelude to the more detailed description that is presented later.

The present invention is directed to a portable non-volatile storage device, comprising, consisting essentially of and/or consisting of: (a) a housing assembly, wherein the housing assembly comprises: at least one sidewall, a top wall, and a bottom wall; and wherein the at least one sidewall, the top wall, and the bottom wall are in a spaced-apart relationship to define an internal chamber therebetween; (b) an electronics assembly positioned at least partially within the housing assembly; and (c) means for providing a patient's medical records regardless of the patient's level of consciousness.

The present invention is also directed to a portable non-volatile storage device, comprising, consisting essentially of and/or consisting of: (a) a housing assembly, wherein the housing assembly comprises: at least one sidewall, a top wall, and a bottom wall; and wherein the at least one sidewall, the top wall, and the bottom wall are in a spaced-apart relationship to define an internal chamber therebetween; and (b) an electronics assembly positioned at least partially within the housing assembly, wherein the electronics assembly comprises: an energy source, a printed circuit board, a memory module, a sound level meter, an accelerometer, a transducer, a light source, and a user interface.

In a preferred embodiment of the present invention, the housing assembly comprises a closed aperture adapted for securement with a lanyard so the storage device may be worn as a necklace.

In another preferred embodiment of the present invention, the energy source comprises a primary electrochemical cell, a secondary electrochemical cell, a capacitor, and/or a fuel cell.

In yet another preferred embodiment of the present invention, the printed circuit board comprises at least one of a battery, a bridge rectifier, a capacitor, a central processing unit, a communications port, a control board, a crystal, a diode, a fuse, a graphics board, an inductor, an input port, an integrated circuit, a microprocessor, a memory module, an oscillator, an output port a potentiometer, a receiver, a relay, a resistor, a semiconductor, a transducer, a transformer, a transistor, a tuner, a video processing unit, a wired communications hub, and a wireless communications hub.

In one preferred embodiment of the present invention, the memory module comprises dynamic random access memory (DRAM), a DRAM buffer, flash memory, a memory controller, and a peripheral component interconnect express (PCIe) bus to connect the storage medium device to a computing device such that a central processing unit (CPU) of the computing device reads data from, and writes data to the DRAM or flash memory.

In a preferred implementation of the present invention, the sound level meter generates an alert signal when a threshold decibel level is observed.

In another preferred implementation of the present invention, the accelerometer generates an alert signal when a threshold change in velocity and/or acceleration is observed.

In yet another preferred implementation of the present invention, the transducer generates an audio alert when an alert signal is generated by the sound level meter and/or the accelerometer.

In a preferred implementation of the present invention, the light source generates a visual alert when an alert signal is generated by at least one of the sound level meter and the accelerometer.

In another preferred implementation of the present invention, the light source comprises a light-emitting diode, an organic light-emitting diode, a tri-color (RGB) light-emitting diode, an incandescent bulb, a tungsten-halogen bulb, a xenon bulb, a fluorescent bulb, a compact fluorescent lamp, and/or a high-intensity discharge bulb.

In yet another preferred implementation of the present invention, the user interface comprises a graphical user interface, a button, a switch, and/or an actuating member that is adapted to manually generate an alert signal.

In a preferred embodiment of the present invention, the storage device further comprises a cap that covers the PCIe bus.

In another preferred embodiment of the present invention, the storage device further comprises a kinetic energy charger.

BRIEF DESCRIPTION OF THE DRAWINGS

Certain embodiments of the present invention are illustrated by the accompanying figures. It will be understood that the figures are not necessarily to scale and that details not necessary for an understanding of the invention or that render other details difficult to perceive may be omitted. It will be further understood that the invention is not necessarily limited to the particular embodiments illustrated herein.

The invention will now be described with reference to the drawings wherein.

DETAILED DESCRIPTION OF THE INVENTION

Figure 1:
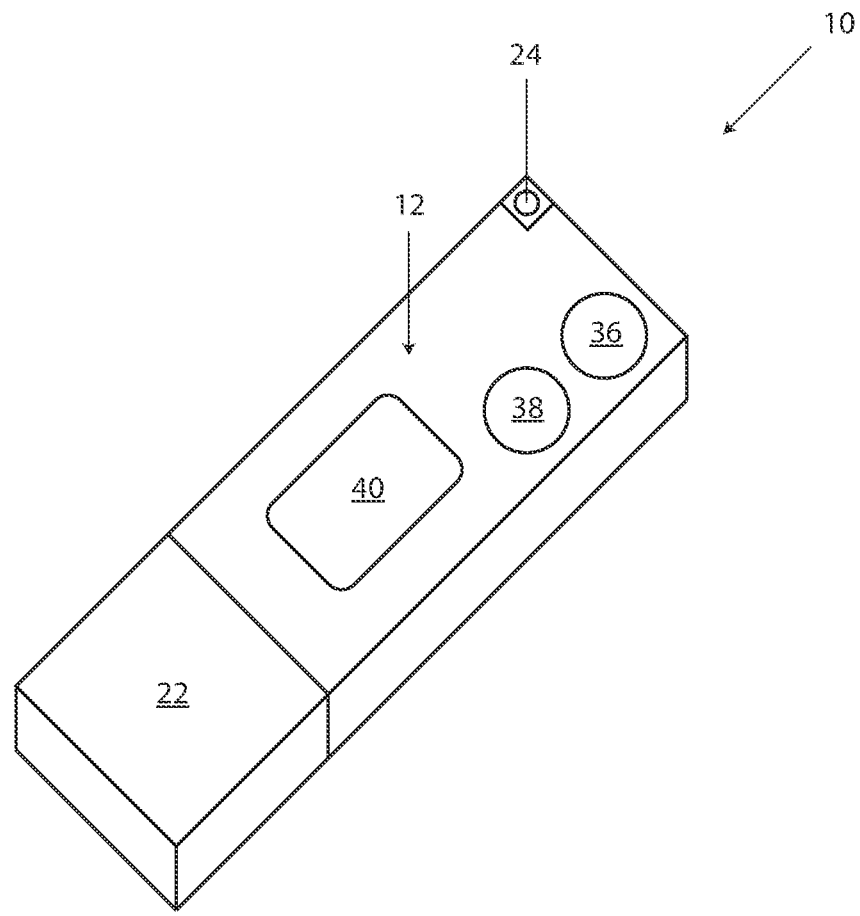
FIG. 1 of the drawings is a front perspective view of a first embodiment of a storage device manufactured in accordance with the present invention.
Figure 2:
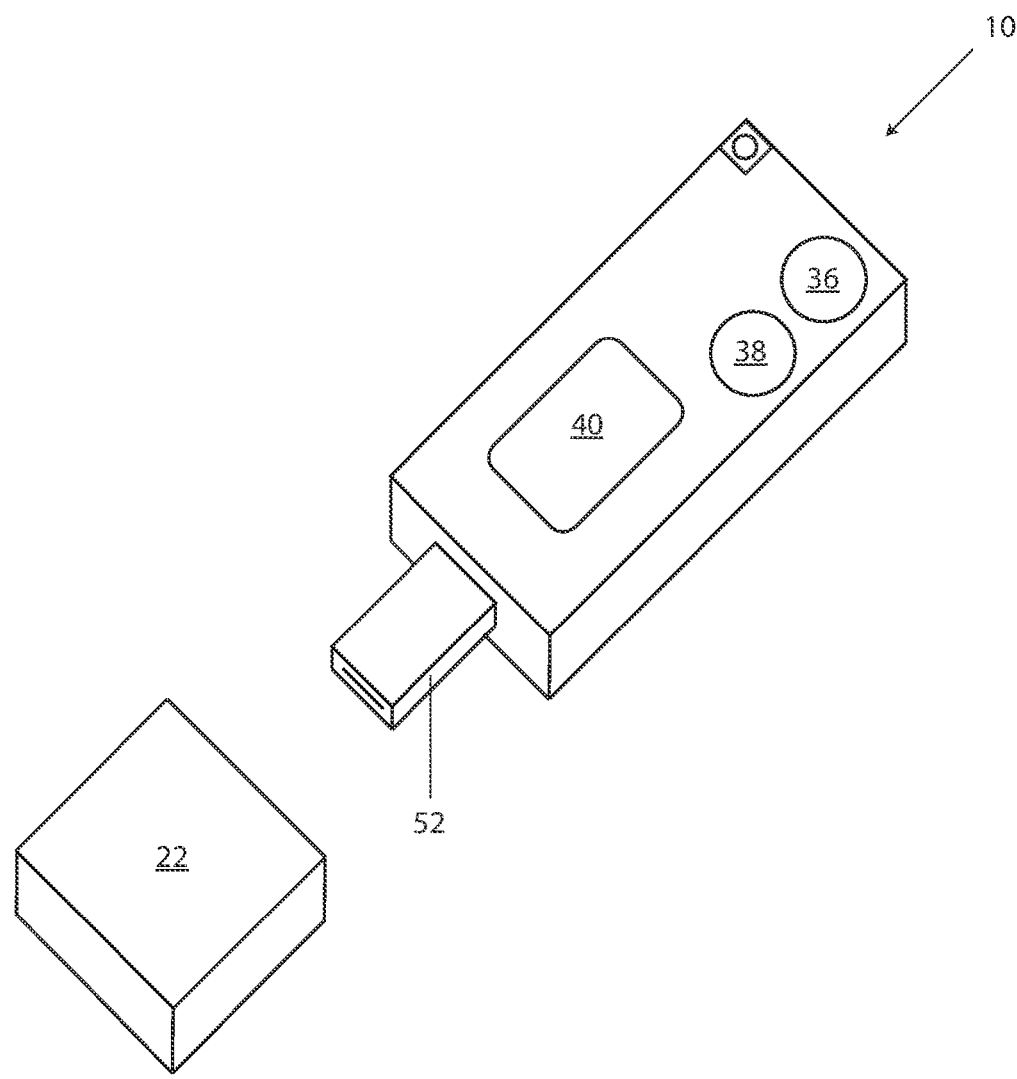
FIG. 2 of the drawings is a front perspective view of the storage device of FIG. 1, showing the cap/protective cover removed and exposing the PCIe bus.
Figure 3:
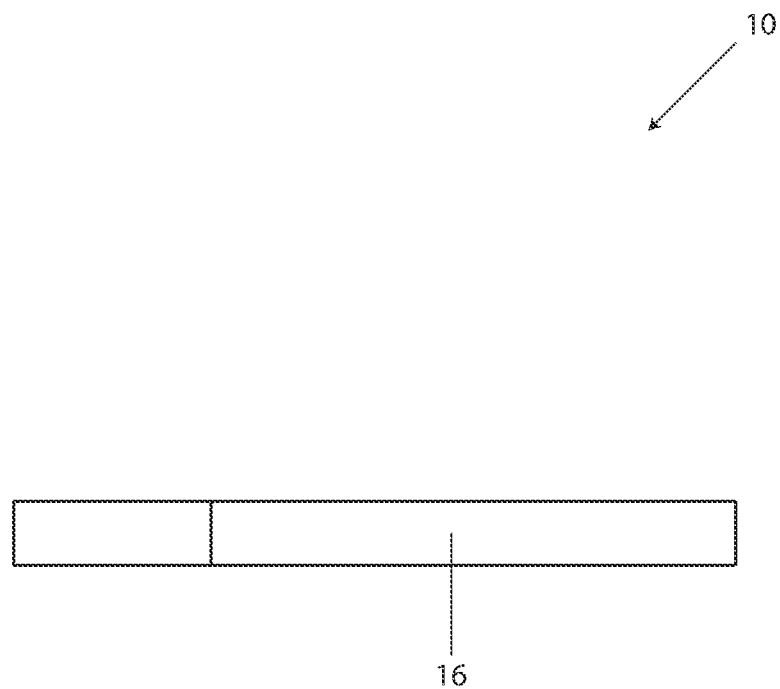
FIG. 3 of the drawings is a left side view of the storage device of FIG. 1.
Figure 4:
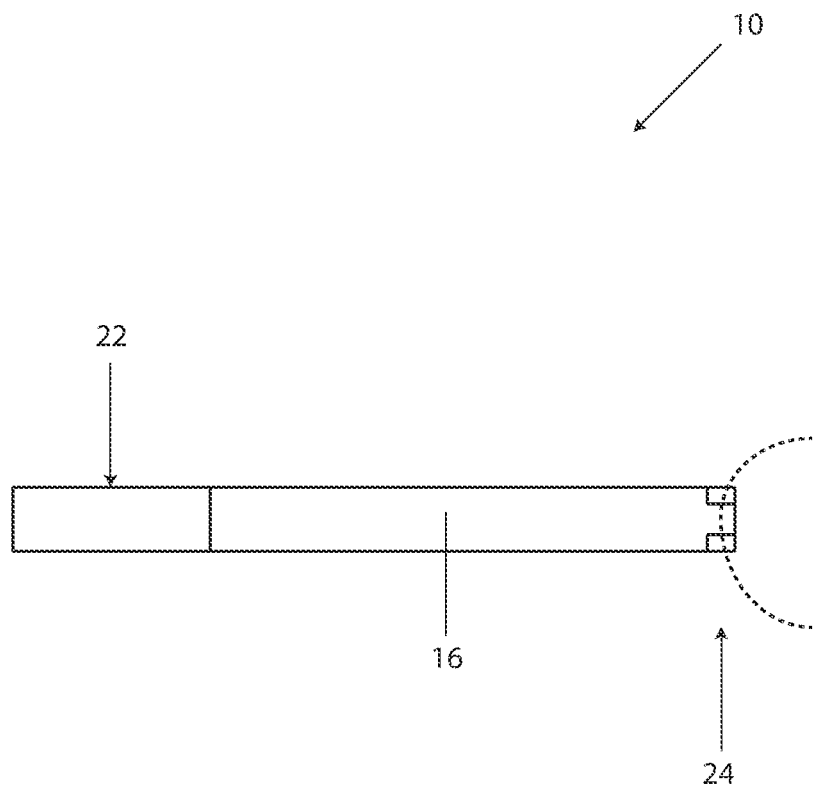
FIG. 4 of the drawings is a right side view of the storage device of FIG. 1.
Figure 5:
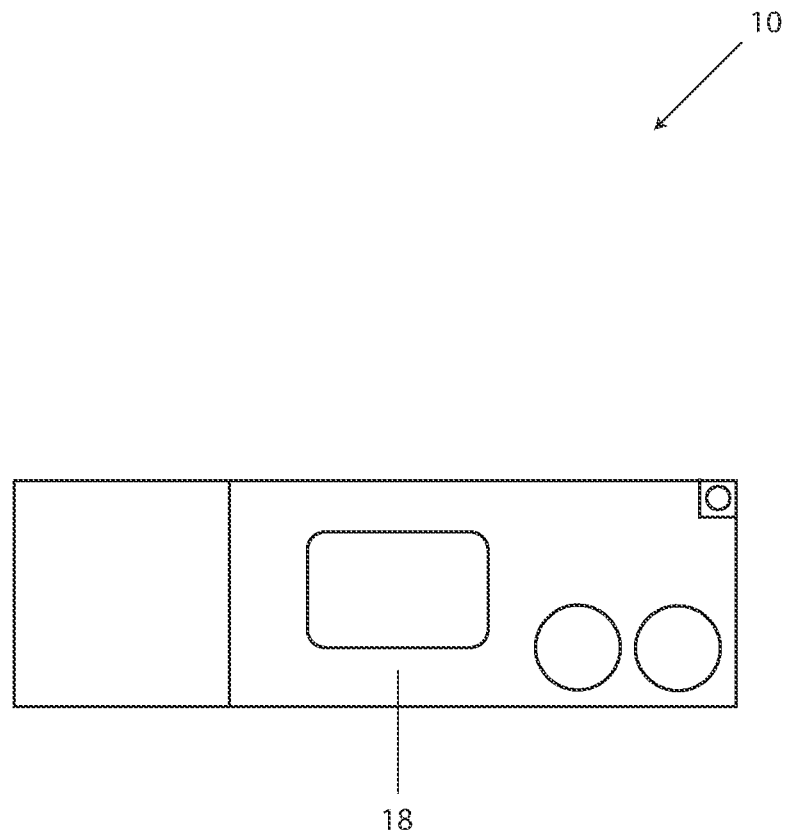
FIG. 5 of the drawings is a top view of the storage device of FIG. 1.

While this invention is susceptible of embodiment in many different forms, there is disclosed and described herein in detail several specific embodiments with the understanding that the present disclosure is to be considered as an exemplification of the principles of the invention and is not intended to limit the invention to the embodiments illustrated.

In general, the present disclosure is directed to non-volatile storage devices (e.g., solid state drives, flash drives, etcetera) that enable a patient to provide a physician with his/her patient information and/or medical records regardless of his/her level of consciousness (e.g., conscious, confused, delirious, somnolent, obtunded, stuporous, comatose, etcetera).

Referring collectively now to FIGS. 1-6, portable non-volatile storage device 10 generally comprises housing assembly 12 and electronics assembly 14 positioned at least partially within the housing assembly. It will be understood that a male PCIe bus extends beyond housing assembly 12. Storage device 10 is configured with means for providing a patient's medical records regardless of the patient's level of consciousness.

In one implementation of the present invention, housing assembly 12 preferably includes one or more sidewall(s) 16, top wall 18, and bottom wall 20. These walls are in a spaced-apart relationship to define an internal chamber therebetween which houses electronics assembly 14—except for a PCIe bus when cap 22 is removed.

Housing assembly 12, also preferably includes closed aperture 24 adapted for securement with a lanyard so the storage device may be worn as a necklace, bracelet, or otherwise adorned by a user.

In one embodiment of the present invention, housing assembly 12 is preferably fabricated from a material selected from the group consisting of a metal, a metal alloy, a natural resin, a synthetic resin, a plastic, a composite, and/or wood and serves to protect the contents of electronics assembly 14.

Figure 6:
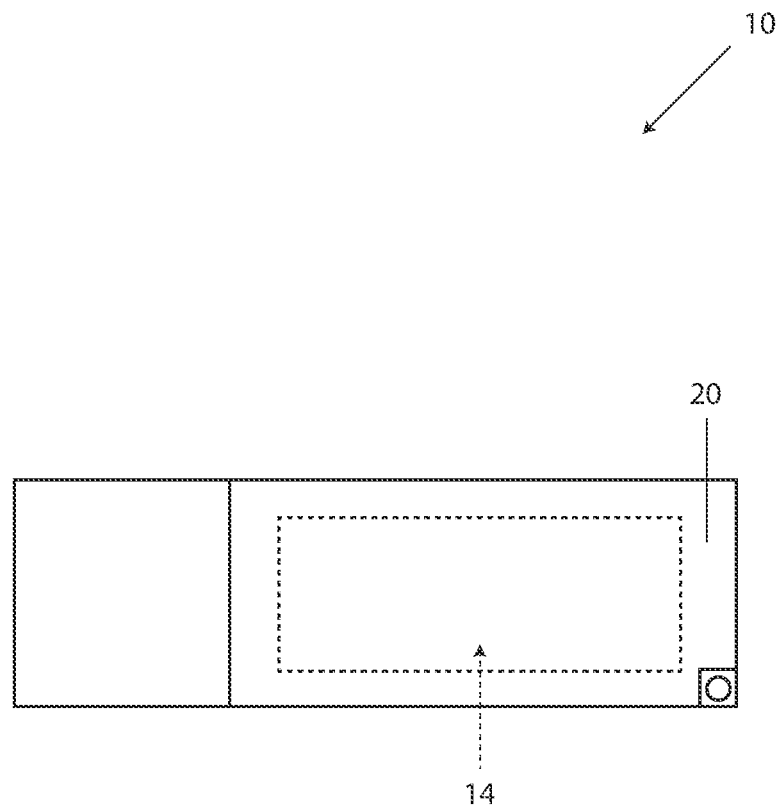
FIG. 6 of the drawings is a bottom view of the storage device of FIG. 1.
Figure 7:
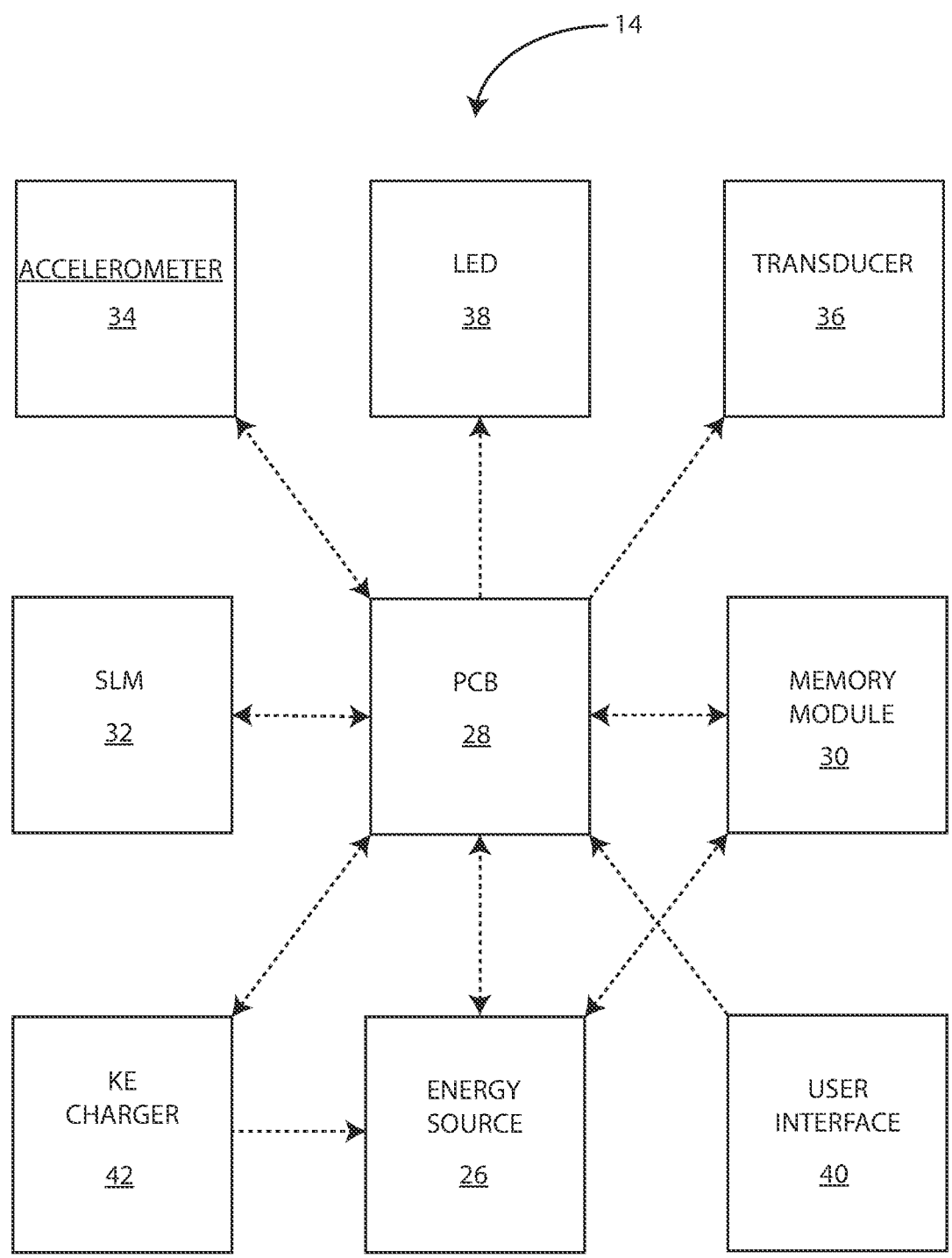
FIG. 7 of the drawings is schematic representation of an electronics assembly, showing unilateral and/or bilateral communication pathways, for use in accordance with the present invention.

As is best shown in FIGS. 6 and 7, in a preferred implementation of the present invention, electronics assembly 14 is positioned at least partially within housing assembly 12 and generally includes energy source 26, printed circuit board 28, memory module 30, sound level meter 32, accelerometer 34, transducer/speaker 36, light source/LED 38, and user interface 40. In certain embodiments, storage device 10 can also include kinetic energy charger 42.

Energy source 26 powers all requisite components of electronics assembly 14 and preferably comprises a primary electrochemical cell, a secondary electrochemical cell, a capacitor, and/or a fuel cell.

Printed circuit board 28 serves as the main controller and communication conduit, and optionally comprises at least one of a battery, a bridge rectifier, a capacitor, a central processing unit, a communications port, a control board, a crystal, a diode, a fuse, a graphics board, an inductor, an input port, an integrated circuit, a microprocessor, a memory module, an oscillator, an output port a potentiometer, a receiver, a relay, a resistor, a semiconductor, a transducer, a transformer, a transistor, a tuner, a video processing unit, a communication modem, a wired communications hub, a GPS unit, and a wireless communications hub.

Memory module 30 stores predetermined patient data, such as, but not limited to, name, age, weight, gender, blood type, next of kin, emergency contacts, medications, medical conditions, medical directives, medical history, historical test and diagnostics, etcetera. It will be understood that such data can be entered via the user/patient and/or caregiver—preferably through CPU data entry via, for example, a PCIe bus.

Figure 8:
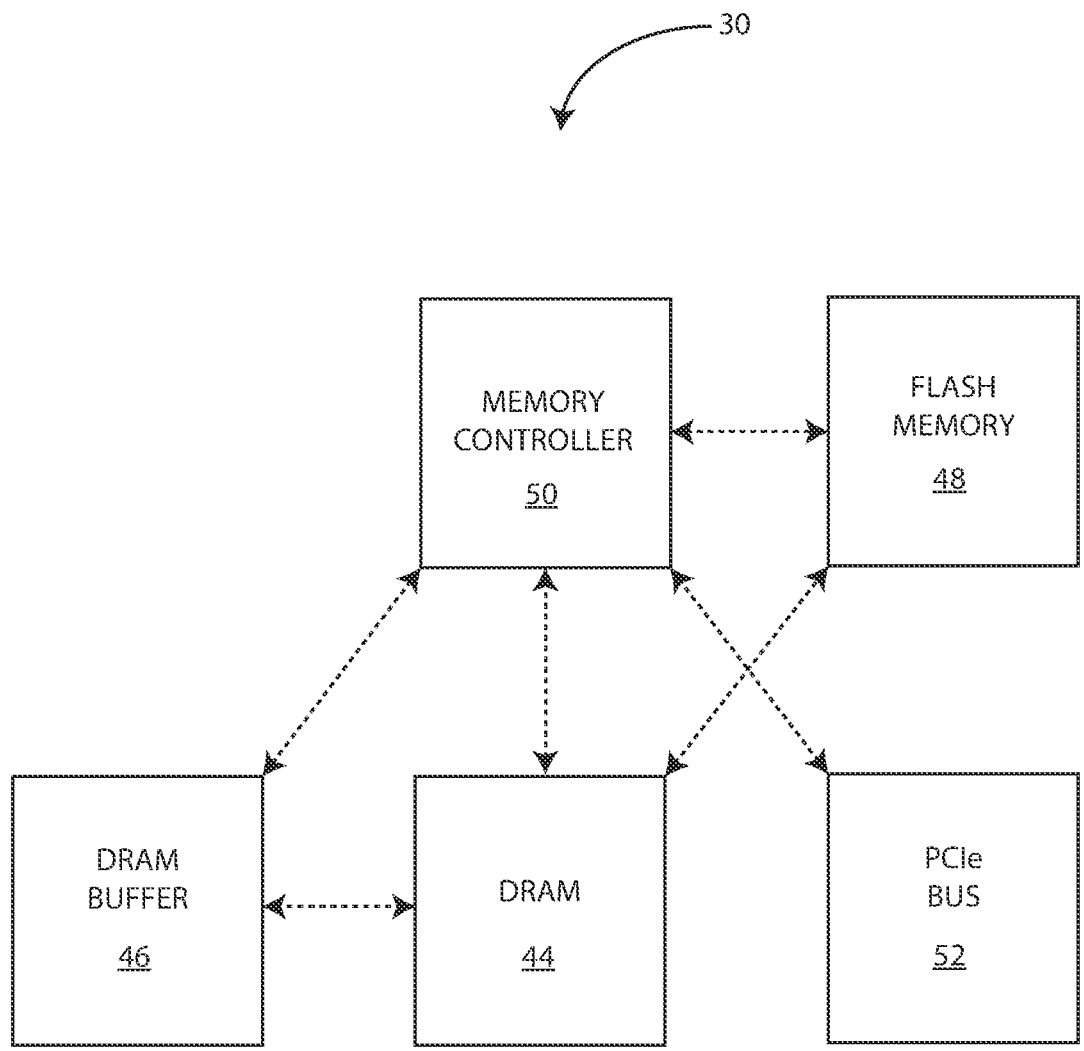
FIG. 8 of the drawings is schematic representation of a memory module assembly, showing unilateral and/or bilateral communication pathways, for use in accordance with the present invention.

As is best shown in FIG. 8, and in one implementation of the present invention, memory module 30 comprises dynamic random access memory (DRAM) 44, DRAM buffer 46, flash memory 48, memory controller 50, and peripheral component interconnect express (PCIe) bus 52 to connect the storage medium device to a computing device such that a central processing unit (CPU) of the computing device reads data from, and writes data to the DRAM or flash memory.

In a preferred embodiment, sound level meter 32 generates an alert signal when a threshold decibel level is observed, such as when a patient slips and falls and/or is in an accident (e.g., auto, motorcycle, etcetera). The alert signal can facilitate an audio (e.g., via transducer/speaker/audio output/alarm 36) and/or visual alarm (e.g., via solid, flashing, and/or strobe light source 38) so that a first responder is aware of the presence of storage device 10. Preferably, storage device 10 includes medical indicia on or more outer surfaces. The alert signal can also facilitate an emergency phone call to, for example, 911.

In another preferred embodiment, accelerometer 34 generates an alert signal when a threshold change in velocity and/or acceleration is observed, such as when a patient slips and falls and/or is in an accident (e.g., auto, motorcycle, etcetera). The alert signal can facilitate an audio (e.g., transducer/speaker) and/or visual alarm (e.g., solids, flashing, and/or strobe LED) so that a first responder is aware of the presence of storage device 10. Preferably, storage device 10 includes medical indicia on or more outer surfaces. The alert signal can also facilitate an emergency phone call to, for example, 911.

In one embodiment of the present invention, an alert signal is only generated if both sound level meter 32 and accelerometer 34 detect a fault or triggering condition within a small window of time (e.g., 1, 2, 3, 4, 5 seconds) to prevent a false positive alarm from occurring.

Light source 38 preferably comprises at least one of a light-emitting diode, an organic light-emitting diode, a tri-color (RGB) light-emitting diode, an incandescent bulb, a tungsten-halogen bulb, a xenon bulb, a fluorescent bulb, a compact fluorescent lamp, and a high-intensity discharge bulb.

User interface 40 allows a user to manually trigger an alert signal when the user is not feeling well and/or otherwise needs medical attention and/or alert a first responder of the presence of their personal and/or medical information. Preferably, user interface 40 comprises at least one of a graphical user interface, a button, a switch, and/or an actuating member that is adapted to manually generate an alert signal—or other functions.

Referring once again to FIGS. 1 and 2, storage device 10 preferably includes cap 22 that covers and protects PCIe bus 52 when not in use or connected to a computer.

Storage device 10, can also be associated with and/or include kinetic energy charger 42 which converts the kinetic energy of an associated user/individual into an electrical current (i.e. direct current and/or alternating current). In one embodiment of the present invention, kinetic energy charger 42 is at least partially positioned within housing assembly 12. Kinetic energy may preferably be converted from linear, torsional, vibrational and/or compressional motion of a user wearing storage device 10. Kinetic energy charger 42 may comprise, for example, a linear kinetic energy charger, a compressional kinetic energy charger, a vibrational kinetic energy charger, or a torsional kinetic energy charger. Preferably, kinetic energy charger 42 will comprise a combination of all the aforementioned kinetic energy chargers to take advantage of all the various types of kinetic energy produced by the individual wearing storage device 10.

In another aspect of the present invention, kinetic energy charger 42 converts the kinetic energy of a user immediately into direct current. In another embodiment of the present invention, kinetic energy charger 42, converts the kinetic energy of a user into alternating current. If kinetic energy charger 42 converts the kinetic energy to alternating current, then storage device 10 may preferably further comprise a rectifier. It will be understood that the rectifier is preferably at least partially positioned within housing assembly 12, and converts alternating current produced by kinetic energy charger 42 into direct current.

In one embodiment of the present invention, energy source and/or storage device 26 receives direct current from a rectifier. In another embodiment, energy source and/or storage device 26 receives direct current from kinetic energy charger 42.

The foregoing description merely explains and illustrates the invention and the invention is not limited thereto except insofar as the appended claims are so limited, as those skilled in the art who have the disclosure before them will be able to make modifications without departing from the scope of the invention.

While certain embodiments have been illustrated and described, it should be understood that changes and modifications can be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms "comprising," "including," "containing," etcetera shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etcetera. As a non-limiting example, each range discussed herein can be readily broken down into a lower third, middle third and upper third, etcetera. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims.

What is claimed and desired to be secured by Letters Patent of the United States is:

1. A portable non-volatile storage device, comprising:
   a housing assembly, wherein the housing assembly comprises:
     at least one sidewall, a top wall, and a bottom wall; and
     wherein the at least one sidewall, the top wall, and the bottom wall are in a spaced-apart relationship to define an internal chamber therebetween;
   an electronics assembly positioned at least partially within the housing assembly, wherein the electronics assembly comprises:
     a memory module storing patient medical records;
     a sound level meter configured to generate a first alert signal when detecting a sound above a threshold decibel level;
     an accelerometer configured to generate a second alert signal when detecting an acceleration above a threshold acceleration value;
     a processor configured to validate an emergency condition only when both the first alert signal and the second alert signal are received within a predetermined time window;
     a transducer configured to generate an audio alert in response to the validated emergency condition; and
     a light source configured to generate a visual alert in response to the validated emergency condition; and
   a closed aperture adapted for securement with a lanyard so the storage device may be worn as a necklace.

2. A portable non-volatile storage device, consisting of:
   a housing assembly consisting of:
     at least one sidewall, a top wall, and a bottom wall defining an internal chamber therebetween; and
     a closed aperture at a top portion of the housing assembly adapted for securement with a lanyard;
   an electronics assembly positioned within the internal chamber, the electronics assembly consisting of:
     an energy source comprising a secondary electrochemical cell;
     a printed circuit board;
     a memory module consisting of:
       dynamic random access memory (DRAM);
       a DRAM buffer;
       flash memory storing patient medical records;
       a memory controller; and
       a peripheral component interconnect express (PCIe) bus;
     a sound level meter configured to generate a first alert signal when a threshold decibel level is detected;
     an accelerometer configured to generate a second alert signal when a threshold acceleration is detected;
     a processor configured to validate an emergency condition only when both the first alert signal and the second alert signal occur within a five second time window;
     a light-emitting diode configured to generate a visual alert in response to the validated emergency condition;
     a transducer configured to generate an audio alert in response to the validated emergency condition; and
     a user interface button configured to manually generate an alert signal; and
   a protective cap removably covering the PCIe bus.

\* \* \* \* \*